(12) United States Patent
Aspinwall et al.

(10) Patent No.: US 12,360,107 B2
(45) Date of Patent: Jul. 15, 2025

(54) SYNTHESIS OF nanoSCINT PARTICLES

(71) Applicant: Arizona Board of Regents on Behalf of the University of Arizona, Tucson, AZ (US)

(72) Inventors: Craig Aspinwall, Tucson, AZ (US); Colleen Janczak, Tucson, AZ (US)

(73) Assignee: ARIZONA BOARD OF REGENTS ON BEHALF OF THE UNIVERISTY OF ARIZONA, Tucson, AZ (US)

( * ) Notice: Subject to any disclaimer, the term of this patent is extended or adjusted under 35 U.S.C. 154(b) by 709 days.

(21) Appl. No.: 17/614,998

(22) PCT Filed: May 29, 2020

(86) PCT No.: PCT/US2020/035370
§ 371 (c)(1),
(2) Date: Nov. 29, 2021

(87) PCT Pub. No.: WO2020/243601
PCT Pub. Date: Dec. 3, 2020

(65) Prior Publication Data
US 2022/0221447 A1    Jul. 14, 2022

Related U.S. Application Data

(60) Provisional application No. 62/855,240, filed on May 31, 2019.

(51) Int. Cl.
*G01N 33/533* (2006.01)
*C08K 5/01* (2006.01)
(Continued)

(52) U.S. Cl.
CPC ............ *G01N 33/533* (2013.01); *C08K 5/01* (2013.01); *C08K 5/3415* (2013.01);
(Continued)

(58) Field of Classification Search
CPC ...... G01N 33/533; G01N 33/542; C08K 5/01; C08K 5/3415; C09K 11/025; C09K 11/06;
(Continued)

(56) References Cited

U.S. PATENT DOCUMENTS 3,799,743 A  3/1974 Barfort
6,855,270 B2  2/2005 Mumper et al.
(Continued)

FOREIGN PATENT DOCUMENTS

WO  WO2013180659 A1  12/2013
WO  WO2015054493 A1  4/2015

OTHER PUBLICATIONS

Wolcke, Julian; Ullmann, Dirk. Drug Discovery Today. 2001, 6, 637-646.
(Continued)

*Primary Examiner* — Dennis White
(74) *Attorney, Agent, or Firm* — NGUYEN TARBET IP LAW (57) ABSTRACT

The present invention provides a process for producing a nanocomposite particle ("nanoSCINT particle") adapted for use in scintillating proximity assay in a relatively high quantity. The nanoSCINT particle comprises a silica shell that encapsulates a nanoparticle organic polymer that is doped with at least one scintillating compound. In particular, the process of the invention includes adding a plurality of batch-wise portions of a polymerization initiator to an emulsion comprising a relatively high amount of polymerizable organic compound to produce a nanoparticle organic polymer, which is then doped with at least one scintillating compound, and then encapsulated with a silica shell to produce nanoSCINT particles in gram quantities in a single process. Unlike conventional methods, a single process of (Continued)

the invention provides at least about 5 g, typically at least about 7.5 g, and often at least about 10 g of nanocomposite particles.

13 Claims, 2 Drawing Sheets

(51) Int. Cl.
    *C08K 5/3415* (2006.01)
    *C09K 11/02* (2006.01)
    *C09K 11/06* (2006.01)
    *G01N 33/542* (2006.01)

(52) U.S. Cl.
    CPC ............ *C09K 11/025* (2013.01); *C09K 11/06* (2013.01); *G01N 33/542* (2013.01); *C09K 2211/1007* (2013.01); *C09K 2211/1018* (2013.01)

(58) Field of Classification Search
    CPC .... C09K 2211/1007; C09K 2211/1018; C09D 183/02; C08L 25/06
    See application file for complete search history.

(56) References Cited

U.S. PATENT DOCUMENTS

| | | | |
|---|---|---|---|
| 2002/0037986 | A1 | 3/2002 | Meier et al. |
| 2004/0171011 | A1 | 9/2004 | Schmitt et al. |
| 2005/0191616 | A1 | 9/2005 | Shenoy et al. |
| 2005/0244453 | A1 | 11/2005 | Stucke et al. |
| 2006/0014013 | A1 | 1/2006 | Saavedra et al. |
| 2007/0116733 | A1 | 5/2007 | Graneli et al. |
| 2010/0068808 | A1 | 3/2010 | Bangera et al. |
| 2014/0316116 | A1 | 10/2014 | Weir et al. |
| 2015/0362600 | A1 | 12/2015 | Perna et al. |
| 2016/0250330 | A1 | 9/2016 | Makale et al. |
| 2018/0118916 | A1* | 5/2018 | Aspinwall ............... C08L 25/06 |

OTHER PUBLICATIONS

Moaddel, Ruin; Wainer, Irving W. Journal of Pharmaceutical and Biomedical Analysis. 2007, 43, 399-406.
Wiedmer, Susanne K.; Jussila, Minttu S.; Riekkola, Marja-Liisa. Trends in Analytical Chemistry. 2004, 23, 562-582.
Lundahl, Per; Yang, Qing. Journal of Chromatography. 1991, 544, 283-304.
Yang, Qing; Liu, Xue-Ying; Ajiki, Shu-Ichi; Hara, Masayuki, et al. Journal of Chromatography B. 1998, 707, 131-141.
Liu, Xue-Ying; Yang, Qing; Nakamura, Chikashi; Miyake, Jun. Journal of Chromatography B. 2001, 750, 51-60.
Krause, Eberhard; Dathe, Margitta; Wieprecht, Torsten; Bienert, Michael. Journal of Chromatography A. 1999, 849, 125-133.
Proverbio, Davide; Roos, Christian; Beyermann, Michael; Orban, Erika, et al. Biochimica et Biophysica Acta. 2013, 1828, 2182-2192.
Yang, Qing; Lundahl, Per. Biochemistry. 1995, 34, 7289-7294.
Moaddel, R.; Rosenberg, A.; Spelman, K.; Frazier, J., et al. Analytical Biochemistry. 2011, 412, 85-91.
Moaddel, Ruin; Wainer, Irving W. Analytica Chimica Acta. 2006, 564, 97-105.
Ross, Eric E.; Bondurant, Bruce; Spratt, Tony; Conboy, John C., et al. Langmuir. 2001, 17, 2305-2307.
Ross, Eric E.; Rozanski, Lynn J.; Spratt, Tony; Liu, Sanchao, et al. Langmuir. 2003, 19, 1752-1765.
Michel, Roger; Subramaniam, Varuni; McArthur, Sally L.; Bondurant, Bruce, et al. Langmuir. 2008, 24, 4901-4906.
Subramaniam, Varuni; D'Ambruoso, Gemma D.; Hall, Henry K., Jr.; Wysocki, Ronald J., Jr., et al. Langmuir. 2008, 24, 11067-11075.
Subramaniam, Varuni; Alves, Isabel D.; Salgado, Gilmar F. J.; Lau, Pick-Wei, et al. Journal of the American Chemical Society. 2004, 127, 5320-5321.
Taillardat-Bertschinger, Agnes; Carrupt, Pierre-Alain; Barbato, Francesco; Testa, Bernard. Journal of Medicinal Chemistry. 2003, 46, 655-665.
Liu, Hanian; Ong, Shaowei; Glunz, Louis; Pidgeon, Charles. Analytical Chemistry. 1995, 67, 3550-3557.
Barbato, F.; Di Martino, G.; Grumetto, L.; La Rotonda, M. I. European Journal of Pharmaceutical Sciences. 2004, 22, 261-269.
Zhang, Yanxiao; Xiao, Yingxian; Kellar, Kenneth J.; Wainer, Irving W. Analytical Biochemistry. 1998, 264, 22-25.
Beigi, Farideh; Wainer, Irving W. Analytical Chemistry. 2003, 75, 4480-4485.
Moaddel, Ruin; Wainer, Irving W. Nature Protocols. 2009, 4, 197-205.
Gottschalk, Ingo; Lagerquist, Caroline; Zuo, Shu-Sheng; Lundqvist, Andreas; Lundahl, Per. Journal of Chromatography B. 2002, 768, 31-40.
Mansfield, Elisabeth; Ross, Eric E.; Aspinwall, Craig A. Analytical Chemistry. 2007, 79, 3135-3141.
Adem, Seid M.; Mansfield, Elisabeth; Keogh, John P.; Hall, Henry K., Jr.; Aspinwall, Craig A. Analytica Chimica Acta. 2013, 772, 93-98.
Ross, Eric E.; Mansfield, Elisabeth; Aspinwall, Craig A. Journal of the American Chemical Society. 2005, 127, 16756-16757.
Lamparski, Henry; Liman, Ulrich; Barry, Judith A.; Frankel, David A., et al. Biochemistry. 1992, 31, 685-694.
Andreolini, Franca; Borra, Claudio; Novotny, Milos. Analytical Chemistry. 1987, 59, 2428-2432.
Maruska, Audrius; Pyell, Ute. Journal of Chromatography A. 1997, 782, 167-174.
Krause, Kerstin; Girod, Marco; Chankvetadze, Bezhan; Blaschke, Gottfried. Journal of Chromatography A. 1999, 837, 51-63.
Abramoff, M. D.; Magelhaes, P. J.; Am, S. J. Biophotonics International. 2004, 11, 36-42.
Gulcev, Makedonka D.; Lucy, Charles A. Analytical Chemistry. 2008, 80, 1806-1812.
Richter, Ralf P.; Berat, Remi; Brisson, Alain R. Langmuir. 2006, 22, 3497-3505.
Sarac, A. S. Progress in Polymer Science. 1999, 24, 1149-1204.
Funasaki, Noriaki; Ishikawa, Seiji; Neya, Saburo. Langmuir. 2000, 16, 5584-5587.
Baker, C. A.; Bright, L. K.; Aspinwall, C. A. Anal. Chem. 2013, 85, 9078-9086.
Kasianowicz, J. J.; Robertson, J. W. F.; Chan, E. R.; Reiner, J. E.; Stanford, V. M. Annu. Rev. Anal. Chem. 2008, 1, 737-766.
Stimberg, V. C.; Bomer, J. G.; Van Uitert, I.; Van Den Berg, A.; Le Gac, S. Small 2013, 9, 1076-1085.
Hirano-Iwata, A.; Oshima, A.; Nasu, T.; Taira, T.; Kimura, Y.; Niwano, M. Supramol. Chem. 2010, 22, 406-412.
Oshima, A.; Hirano-Iwata, A.; Mozumi, H.; Ishinari, Y.; Kimura, Y.; Niwano, M. Anal. Chem. 2013, 85, 4363-4369.
Meier, W.; Graff, A.; Diederich, A.; Winterhalter, M. Phys Chem Chem Phys 2000, 2, 4559-4562.
Jeon, T. J.; Malmstadt, N.; Schmidt, J. J. J. Am. Chem. Soc. 2006, 128, 42-43.
Zhang, H.; Joubert, J. R.; Saavedra, S. S. Adv. Polym. Sci. 2010, 224, 1-42.
White, R. J.; Ervin, E. N.; Yang, T.; Chen, X.; Daniel, S.; Cremer, P. S.; White, H. S. J. Am. Chem. Soc. 2007, 129, 11766-11775.
Bright, L. K.; Baker, C. A.; Agasid, M. T.; Ma, L.; Aspinwall, C. A. ACS Appl. Mater. Interfaces 2013, 5, 11918-11926.
Heitz, B. A.; Jones, I. W.; Hall, H. K.; Aspinwall, C. A.; Saavedra, S. S. J. Am. Chem. Soc. 2010, 132, 7086-7093.
Benz, R.; Elbert, R.; Prass, W.; Ringsdorf, H. Eur. Biophys. J. 1986, 14, 83-92.
O'Brien, D. F.; Armitage, B.; Benedicto, A.; Bennett, D. E.; Lamparski, H. G.; Lee, Y.-S.; Srisiri, W.; Sisson, T. M. Acc. Chem. Res. 1998, 31, 861-868.
Daly, S. M.; Heffernan, L. A.; Barger, W. R.; Shenoy, D. K. Langmuir 2005, 22, 1215-1222.
Montal, M.; Mueller, P. Proc. Nat. Acad. Sci. USA 1972, 69, 3561-3566.
Plant, A. L. Langmuir 1999, 15, 5128-5135.

(56) References Cited

OTHER PUBLICATIONS

Gallagher, E. S.; Adem, S. M.; Bright, L. K.; Calderon, I. A. C.; Mansfield, E.; Aspinwall, C. A. Electrophoresis 2014, 35, 1099-1105.

Glaser, R. W.; Leikin, S. L.; Chernomordik, L. V.; Pastushenko, V. F.; Sokirko, A. I. Biochim. Biophys. Acta 1988, 940, 275-287.

Chernomordik, L. V.; Sukharev, S. I.; Abidor, I. G.; Chizmadzhev, Y. A. Bioelectrochem. Bioenerg. 1982, 9, 149-155.

Lundbaek, J. A. J. Gen. Physiol. 2008, 131, 421-429.

Rudnev, V. S.; Ermishkin, L. N.; Fonina, L. A.; Rovin, Y. G. Biochim. Biophys. Acta 1981, 642, 196-202.

Montal, et al. "Formation of Bimolecular Membranes from Lipid Monolayers and a Study of Their Electrical Properties." Proceedings of the National Academy of Sciences [online], Dec. 1972 [Retrieved on Sep. 23, 2015], vol. 69, No. 12, pp. 3561-3566, Retrieved from the Internet: <URL: http://www.pnas.org/contentl69/12/3561.short>.

Joubert, James R.; Smith, Kathryn A.; Johnson, Erin; Keogh, John P., et al. "Stable, Ligand-Doped, Poly(bis-SorbPC) Lipid Bilayer Arrays for Protein Binding and Detection," ACS Applied Materials & Interfaces, vol. 1, No. 6, 1310-1315, 2009.

Liang, Boying; Ju, Yue; Joubert, James R .; Kaleta, Erin J.; et al. "Label-free detection and identification of protein ligands captured by receptors in a polymerized planar lipid bilayer using MALDI-TOF MS," Anal Bioanal Chem, (2015) 407:2777-2789.

Gallagher, Elyssia S.; Adem, Seid M.; Baker, Christopher A.; Ratnayaka, Saliya N.; et al. "Highly stabilized, polymer-lipid membranes prepared on silica microparticles as stationary phases for capillary chromatography," Journal of Chromatography A, (2015).

Cheng, Zhiliang and Aspinwall, Craig A.. "Nanometre-sized molecular oxygen sensors prepared from polymer stabilized phospholipid vesicles," Analyst, 2006, 131,236-243.

Roberts, David L.; Ma, Yaning; Bowles, Steven E.; Janczak, Colleen M.; et al. "Polymer-Stabilized Phospholipid Vesicles with a Controllable, pH-Dependent Disassembly Mechanism," Langmuir 2009, 25, 1908-1910.

Gallagher, Elyssia S.; Mansfield, Elisabeth; Aspinwall, Craig A.. "Stabilized phospholipid membranes in chromatography: toward membrane protein-functionalized stationary phases," Anal Bioanal Chern (2014) 406:2223-2229.

Alberts B, Johnson A, Lewis J, et al. Molecular Biology of the Cell. 4th edition. New York: Garland Science; 2002. National Center for Biotechnology Information; website; accessed on Jun. 18, 2014; http://www.ncbi.nlm.nih.gov/books/NBK26871/.

Meier, Polymer nanocapsules, Jul. 2000, Chem. Soc. Review, Issue 29, pp. 295-303 (Year: 2000).

Graff et al., Nanoreactors from Polymer-Stabilized Liposomes, Jan. 2001, 17(3), pp. 919-923 (Year: 2001).

Heitz et al., Polymerized Planar Suspended Lipid Bilayers for Single Ion Channel Recordings: Comparison of Several Dienoyl Lipids ,Jan. 2011, Langmuir, 27(5), pp. 1882-1890 (Year: 2011).

Supporting Information, 2013 (no month), Journal of Materials Chemistry BSupporting Information, 2013 (no month), Journal of Materials Chemistry B (Year: 2013).

Okazaki et al, Creation of a polymer backbone in lipid bilayer membrane-based nanotubes for morphilogical and microenvironmental stabilization07/24 (Year 2014).

Janczak; Hybrid Nanoparticles for Enhanced Sensitivity in Biological Labeling and Bio-molecular Sensing, 2011.

Choi et al. "Micropatterning Polydiacetylene Supramolecular Vesicles on Glass Substrates using a Pre-Patterned Hydrophobic Thin Filrn" 2012, Macrornol. Chern. Phys. 213, 610-616 (Year: 2012).

Kung et al. "Patterning Hybrid Surfaces of Proteins and Supported Lipid Bilayers" Langrnuir 2000, 16, 6773-6776 (Year: 2000).

Wang and Cheng. "Enhancernent of Binding Kinetics on Affinity Substrates by Laser Point Heating Induced Transport" Analyst, 2016,141, 1807-1813, Supporting Information (Year: 2016).

Stadler et al. "Creation of a functional heterogeneous vesicle array via DNA controlled surface sorting onto a spotted microarray", Dec. 2006, Biointerphases, vol. 1, No. 4, 142-145 (Year: 2006).

Wagner et al. "Tethered Polymer-Supported Planar Lipid Bilayers for Reconstitution of Integral Membrane Proteins: Silane-Polyethyleneglycol-Lipid as a Cushion and Covalent Linker". Sep. 2000. Biophysical Journal, vol. 79,1400-1414 (Year: 2000).

Maria et al. Biomimetic nanoparticles: preparation, characterization and biomedical applications. International Journal of Nanomedicine 2010, Vo1.5, pp. 249-259. (Year: 2010).

Pan et al. "Molecular Recognition and Colorimetric Detection of Cholera Toxin by Poly(diacetylene) Liposomes Incorporating Gml Ganglioside" Center for advanced Materials, Materials Sciences Division, Lawrence Berkley Laboratory, Berkeley, California. vol. 13, No. 6. pp. 1365-1366. May 28, 1996.

Yoshina-Ishii et ai, "Arrays of Mobile Tethered Vesicles on Supported Lipid Bilayers," 2003. J. Am. Chem. Soc. vol. 125, No. 13, 3696-3697 (Year: 2003).

Raymond et al. Functional expression of human 5-HT1A receptors and differential coupling to second messengers in SCH cells. Naunyn-Schmiedeberg Arch Pharmacol 1992, vol. 346, pp. 127-137. (Year: 1992).

Kelkar, D. A.; Chattopadhyay, A. Biochim. Biophys. Acta 2007, 1768,2011-2025.

Jiang et al. "Development and evaluation of a polydiacetylene based biosensor for the detection of H5 influenza virus"; Journal of Virological Methods 219 (2015) 38-45. (Year: 2015).

Pabst et al. "Light-driven proton transport of bacteriorhodopsin incorporated into long-term stable liposomes of a polymerizable sulfolipid"; FEBS Letters, vol. 154, No. 1, Apr. 1983, pp. 5-9 (Year: 1983).

Kim, V., et al. {2012) Synthetic biomimetic membranes and their sensor applications Sensors 12; 9530-9550.

Alderton, W.; Boyhan, A.; Lowe, P. Biochem. J 1998, 332, 195.

Amarnath, K.; Amarnath, V.; Amarnath, K.; Valentine, H. L.; Valentine, W. M., A specific HPLC-UV method for the determination of cysteine and related aminothiols in biological samples. Talanta 2003, 60 (6), 1229-1238.

Bald, E.; Chwatko, G.; Głowacki, R.; Kuśmierek, K., Analysis of plasma thiols by high-performance liquid chromatography with ultraviolet detection. Journal of Chromatography A 2004, 1032 (1-2), 109-115.

Barashkova, I.; Ivanov, V. Polym. Degrad. Stab. 1998, 60, 339.

Barlett A., Lloyd-Jones J., Rance M., Flockhart I., Dockray G., Bennett M. and Moore R., Eur. J. Clin. Pharmacol., 1980, 18, 339-345.

Bartberger, M. D.; Fukuto, J. M.; Houk, K. N., On the acidity and reactivity of HNO in aqueous solution and biological systems. Proceedings of the National Academy of Sciences of the United States of America 2001, 98 (5), 2194-2198.

Bayerl, T.; Bloom, M., Physical properties of single phospholipid bilayers adsorbed to micro glass beads. Biophys. J 1990, 58, 357-362.

Behnke, T. W., Christian; Hoffmann, Katrin; Hübner, Martin; Panne, Ulrich; Ute Resch-Genger J. Fluoresc., 2011, 21, 937-944.

Bosworth, N.; Towers, P., Scintillation proximity assay. Nature 1989, 341, 167-168.

Brandish, P.; Hill, L.; Zheng, W.; Scolnick, E. Anal. Biochem 2003, 313, 311.

Brooks F., Nucl. Instrum. Methods, 1979, 162, 477-505.

Bross A., Nucl. Instrum. Methods Phys. Res., Sect. A, 1990, 295, 315-322.

Buranda, T.; Huang, J.; Ramarao, G.; Ista, L.; Larson, R.; Ward, T.; Sklar, L.; Lopez, G., Biomimetic Molecular Assemblies on Glass and Mesoporous Silica Microbeads for Biotechnology. Langmuir 2003, 19, 1654-1663.

Burns, J. A.; Butler, J. C.; Moran, J.; Whitesides, G. M., Selective reduction of disulfides by tris(2-carboxyethyl)phosphine. The Journal of Organic Chemistry 1991, 56 (8), 2648-2650.

Calvo, M., Gundberg, C., Heath, H. and Fox, J., Am. J. Physiol. Endocrinol. Metab., 1991, 261, E262-E268.

Chen, L.-C.; Casadevall, A., Labeling of Proteins with [35S]Methionine and/or [35S]Cysteine in the Absence of Cells. Analytical Biochemistry 1999, 269 (1), 179-188.

(56) References Cited

OTHER PUBLICATIONS

Chen, X.; Ko, S.-K.; Kim, M. J.; Shin, I.; Yoon, J., A thiol-specific fluorescent probe and its application for bioimaging. Chemical Communications 2010, 46 (16), 2751-2753.
Comini, M. A., Measurement and meaning of cellular thiol:disulfhide redox status. Free Radical Research 2016, 50 (2), 246-271.
Cook, N. Reviews 1996, 1, 287.
Dance, I. G., The structural chemistry of metal thiolate complexes. Polyhedron 1986, 5 (5), 1037-1104.
Davies, K. J. A., Oxidative stress: the paradox of aerobic life. Biochemical Society Symposia 1995, 61, 1-31.
Derenzo, S.; Weber, M.; Bourret-Courchesne, E.; Klintenberg, M. Nucl. Instrum. Methods Phys. Res., Sect. A. 2003, 505, 111.
Derjaguin B. V., Pure and Appl. Chem. , 1976, 48, 387-392.
Destruel, P., Taufer, M., D'Ambrosio, C., Da Via, C., Fabre, J., Kirkby, J. and Leutz, H., Nucl. Instrum. Methods Phys. Res., Sect. A, 1989, 69-77.
Doctorovich, F.; Bikiel, D.; Pellegrino, J.; Suárez, S. A.; Larsen, A.; Martí, M. A., Nitroxyl (azanone) trapping by metalloporphyrins. Coordination Chemistry Reviews 2011, 255 (23-24), 2764-2784.
Dorn, P., Salanitro, J. and Evan, S., Environmental Toxicology and Chemistry, 1993, 12, 1751-1762.
Doyle, M. P.; Mahapatro, S. N.; Broene, R. D.; Guy, J. K., Oxidation and reduction of hemoproteins by trioxodinitrate(II). The role of nitrosyl hydride and nitrite. Journal of the American Chemical Society 1988, 110 (2), 593-599.
Dröge, W.; Eck, H. P.; Mihm, S., HIV-induced cysteine deficiency and T-cell dysfunction—a rationale for treatment with N-acetylcysteine. Immunology Today 1992, 13 (6), 211-214.
Dutton, A. S.; Fukuto, J. M.; Houk, K. N., Mechanisms of HNO and NO Production from Angeli's Salt: Density Functional and CBS-QB3 Theory Predictions. Journal of the American Chemical Society 2004, 126 (12), 3795-3800.
Egwim, I. O. C.; Gruber, H. J., Spectrophotometric Measurement of Mercaptans with 4,4'-Dithiodipyridine. Analytical Biochemistry 2001, 288 (2), 188-194.
Fernandes, P. A.; Ramos, M. J., Theoretical Insights into the Mechanism for Thiol/Disulfide Exchange. Chemistry 2004, 10 (1), 257-266.
Flammersfeld, A. Naturewissenschaften 1947, 33, 280.
Fritz G., Schadler V., Willenbacher N. and Wagner N., Langmuir, 2002, 18, 6381-6390.
Fritz H., Maier M. and Bayer E., J. Colloid Interface Sci., 1997, 195, 272-288.
Fukuto, J. M.; Bianco, C. L.; Chavez, T. A., Nitroxyl (HNO) signaling. Free Radical Biology and Medicine 2009, 47 (9), 1318-1324.
García-Beltrán, O.; Mena, N.; Pérez, E. G.; Cassels, B. K.; Nuñez, M. T.; Werlinger, F.; Zavala, D.; Aliaga, M. E.; Pavez, P., The development of a fluorescence turn-on sensor for cysteine, glutathione and other biothiols. A kinetic study. Tetrahedron Letters 2011, 52 (49), 6606-6609.
Getz, E. B.; Xiao, M.; Chakrabarty, T.; Cooke, R.; Selvin, P. R., A Comparison between the sulfhydryl reductants tris(2-carboxyethyl)phosphine and dithiothreitol for use in protein biochemistry. Analytical Biochemistry 1999, 273 (1), 73-80.
Gilbert, H. F., Molecular and Cellular Aspects of Thiol-Disulfide Exchange. In Advances in Enzymology and Related Areas of Molecular Biology, John Wiley & Sons, Inc.: 2006; pp. 69-172.
Glickman, J., Schmid A. and Ferrand S., Assay and Drug Development Technologies, 2008, 6, 433-455.
Graff, A.; Winterhalter, M.; Meier, W., Nanoreactors from Polymer-Stabilized Liposomes. Langmuir 2001, 17, 919-923.
Guan, X.; Hoffman, B.; Dwivedi, C.; Matthees, D. P., A simultaneous liquid chromatography/mass spectrometric assay of glutathione, cysteine, homocysteine and their disulfides in biological samples. Journal of Pharmaceutical and Biomedical Analysis 2003, 31 (2), 251-261.

Hansen, R. E.; Østergaard, H.; Nørgaard, P.; Winther, J. R., Quantification of protein thiols and dithiols in the picomolar range using sodium borohydride and 4,4'-dithiodipyridine. Analytical Biochemistry 2007, 363 (1), 77-82.
Hansen, R. E.; Roth, D.; Winther, J. R., Quantifying the global cellular thiol-disulfide status. Proceedings of the National Academy of Sciences of the United States of America 2009, 106 (2), 422-427.
Hansen, R. E.; Winther, J. R., An introduction to methods for analyzing thiols and disulfides: Reactions, reagents, and practical considerations. Analytical Biochemistry 2009, 394 (2), 147-158.
Harder, D.; Fotiadis, D., Measuring substrate binding and affinity of purified membrane transport proteins using the scintillation proximity assay. Nature Protocols 2012, 7 (9), 1569-1578.
Hart, H.; Greenwald, E. J. Nucl. Med 1979, 20, 1062.
Hart, H.; Greenwald, E. Mol. Immunol 1979, 16, 265.
Heafield, M. T.; Fearn, S.; Steventon, G. B.; Waring, R. H.; Williams, A. C.; Sturman, S. G., Plasma cysteine and sulphate levels in patients with motor neurone, Parkinson's and Alzheimer's disease. Neuroscience Letters 1990, 110 (1-2), 216-220.
Heise, C.; Sullivan, S.; Crowe, P., Scintillation Proximity Assay as a High-Throughput Method to Identify Slowly Dissociating Nonpeptide Ligand Binding to the GnRH Receptor. J. Biomol. Screening 2007, 12, 235-239.
Hubert, D.; Jung, M.; German, A., Vesicle Templating. Adv. Mater 2000, 12, 1291-1294.
Ithakissios D., Kubiatowicz D. and Wicks J., Clin. Chem., 1980, 26, 323-326.
Jacob, N.; Bruckert, E.; Giral, P.; Foglietti, M. J.; Turpin, G., Cysteine is a cardiovascular risk factor in hyperlipidemic patients. Atherosclerosis 1999, 146 (1), 53-59.
Johnson, G. M.; Chozinski, T. J.; Gallagher, E. S.; Aspinwall, C. A.; Miranda, K. M., Glutathione sulfinamide serves as a selective, endogenous biomarker for nitroxyl after exposure to therapeutic levels of donors. Free Radical Biology and Medicine 2014, 76, 299-307.
Jones, D. P.; Carlson, J. L.; Mody, V. C.; Cai, J.; Lynn, M. J.; Sternberg Jr, P., Redox state of glutathione in human plasma. Free Radical Biology and Medicine 2000, 28 (4), 625-635.
Jones, D. P.; Go, Y.-M.; Anderson, C. L.; Ziegler, T. R.; Kinkade, J. J. M.; Kirlin, W. G., Cysteine/cystine couple is a newly recognized node in the circuitry for biologic redox signaling and control. The FASEB Journal 2004, 18 (11), 1246-1248.
Jung, H. S.; Han, J. H.; Pradhan, T.; Kim, S.; Lee, S. W.; Sessler, J. L.; Kim, T. W.; Kang, C.; Kim, J. S., A cysteine-selective fluorescent probe for the cellular detection of cysteine. Biomaterials 2012, 33 (3), 945-953.
Jung, H. S.; Pradhan, T.; Han, J. H.; Heo, K. J.; Lee, J. H.; Kang, C.; Kim, J. S., Molecular modulated cysteine- selective fluorescent probe. Biomaterials 2012, 33 (33), 8495-8502.
Jung, M.; Ouden, I.; Montoya-Goni, A.; Hubert, D.; Frederik, P.; Van Herk, A.; German, A., Polymerization in Polymerizable Vesicle Bilayer Membranes. Langmuir 2000, 16, 4185-4195.
Kauffman, J., Radiat. Phys. Chem., 1993, 41, 365-371.
Kleinman, W. A.; Richie Jr, J. P., Status of glutathione and other thiols and disulfides in human plasma. Biochemical Pharmacology 2000, 60 (1), 19-29.
Kleinman, W. A.; Richie, J. P., Determination of thiols and disulfides using high-performance liquid chromatography with electrochemical detection. Journal of Chromatography B: Biomedical Sciences and Applications 1995, 672 (1), 73-80.
Knop, G.; Paul, W. In Alpha-, Beta-, and Gamma-Ray Spectroscopy; 1 ed.; Siegbahn, K., Ed.; North-Holland Publishing Company: New York, 1968, p. 1.
Kobayashi, M., Juillerat, F. D. R., Galletto, P., Bowen, P. and Borkovec, M., Langmuir, 2005, 21, 5761-5769.
Kohan, L. M., Sanguanmith, S., Meesungnoen, J., Causey, P., Stuart, C. R. and Jay-Gerin, J.-P., Rsc Adv., 2013, 3, 19282-19299.
Korde, U. Pandey, S. Banerjee, H. Sarma, S. Hajare, M. Venkatesh, A. Sharma and M. Pillai, J. Agric. Food Chem., 2003, 51, 843-846.
Kurja, J.; Nolte, R.; Maxwell, I.; German, A., Free radical polymerization of styrene in dioctadecyldimethylammonium bromide vesicles. Polymer 1993, 34, 2045-2049.

(56) References Cited

OTHER PUBLICATIONS

Kuśmierek, K.; Głowacki, R.; Bald, E., Analysis of urine for cysteine, cysteinylglycine, and homocysteine by high-performance liquid chromatography. Analytical and Bioanalytical Chemistry 2006, 385 (5), 855-860.

Lan, M.; Wu, J.; Liu, W.; Zhang, H.; Zhang, W.; Zhuang, X.; Wang, P., Highly sensitive fluorescent probe for thiols based on combination of PET and ESIPT mechanisms. Sensors and Actuators B: Chemical 2011, 156 (1), 332-337.

Landfester, K., Bechthold, N., Tiarks, F. and Antonietti, M., Macromolecules, 1999, 32, 2679-2683.

Landfester, K., Willert, M. and Antonietti, M., Macromolecules, 2000, 33, 2370-2376.

L'Annunziata, M. F., Chapter 16—Solid Scintillation Analysis. In Handbook of Radioactivity Analysis (Third Edition), Academic Press: Amsterdam, 2012; pp. 1021-1115.

L'Annunziata, M. F.; Kessler, M. J., Chapter 7—Liquid Scintillation Analysis: Principles and Practice. In Handbook of Radioactivity Analysis (Third Edition), Academic Press: Amsterdam, 2012; pp. 423-573.

Lee, J., Hong, C., Choe, S. and Shim, S., J. Colloid Interface Sci., 2007, 310, 112-120.

Lee, J.-H., Gomez, I. J., Sitterle, V. B. and Meredith, J. C., J. Colloid and Interface Sci., 2011, 363, 137-144.

Leichert, L. I.; Jakob, U., Global Methods to Monitor the Thiol-Disulfide State of Proteins In Vivo. Antioxidants & Redox Signaling 2006, 8 (5-6), 763-772.

Lewis, M., Wat. Res., 1991, 25, 101-113.

Loidl-Stahlhofen, A.; Schmitt, J.; Nöller, J.; Hartmann, T.; Brodowsky, H.; Schmitt, W.; Keldenich, J., Solid-Supported Biomolecules on Modified Silica Surfaces—A Tool for Fast Physicochemical Characterization and High-Throughput Screening. Adv. Mater 2001, 13 (23), 1829-1834.

Lopachin, R. M.; Gavin, T., Reactions of electrophiles with nucleophilic thiolate sites: relevance to pathophysiological mechanisms and remediation. Free Radical Research 2016, 50 (2), 195-205.

Lu, J.; Sun, C.; Chen, W.; Ma, H.; Shi, W.; Li, X., Determination of non-protein cysteine in human serum by a designed BODIPY-based fluorescent probe. Talanta 2011, 83 (3), 1050-1056.

Lu, Y., J. McLellan and Y. Xia, Langmuir, 2004, 20, 3464-3470.

Magera, M. J.; Lacey, J. M.; Casetta, B.; Rinaldo, P., Method for the Determination of Total Homocysteine in Plasma and Urine by Stable Isotope Dilution and Electrospray Tandem Mass Spectrometry. Clinical Chemistry 1999, 45 (9), 1517-1522.

Mansoor, M. A.; Bergmark, C.; Svardal, A. M.; Lønning, P. E.; Ueland, P. M., Redox Status and Protein Binding of Plasma Homocysteine and Other Aminothiols in Patients With Early-Onset Peripheral Vascular Disease: Homocysteine and Peripheral Vascular Disease. Arteriosclerosis, Thrombosis, and Vascular Biology 1995, 15 (2), 232-240.

Mia A. and Phillips R., Nature, 1965, 206, 100-101.

Morgan, J.; Johnson, C.; Kaler, E., Polymerization of Equilibrium Vesicles. Langmuir 1997, 13, 6447-6451.

Moriarty-Craige, S. E.; Jones, D. P., Extracellular thiols and thiol/disulfide redox in metabolism. Annual Review of Nutrition 2004, 24 (1), 481-509.

Mornet, S.; Lambert, O.; Duguet, E.; Brisson, A., The Formation of Supported Lipid Bilayers on Silica Nanoparticles Revealed Cryoelectron Microscopy. Nano Lett 2005, 5 (2), 281-285.

Mueller, A.; O'Brien, D., Supramolecular Materials via Polymerization of Mesophases of Hydrated Amphiphiles. Chem. Rev 2002, 102, 727-757.

Nagasawa, H. T.; Demaster, E. G.; Redfern, B.; Shirota, F. N.; Goon, D. J. W., Evidence for nitroxyl in the catalase-mediated bioactivation of the alcohol deterrent agent cyanamide. Journal of Medicinal Chemistry 1990, 33 (12), 3120-3122.

Nagy, P., Kinetics and Mechanisms of Thiol-Disulfide Exchange Covering Direct Substitution and Thiol Oxidation-Mediated Pathways. Antioxidants & Redox Signaling 2012, 18 (13), 1623-1641.

Nair, D. P.; Podgórski, M.; Chatani, S.; Gong, T.; Xi, W.; Fenoli, C. R.; Bowman, C. N., The Thiol-Michael Addition Click Reaction: A Powerful and Widely Used Tool in Materials Chemistry. Chemistry of Materials 2014, 26 (1), 724-744.

Nare, B.; Allocco, J.; Kuningas, R.; Galuska, S.; Myers, R.; Bednarek, M.; Schmatz, D., Devlopment of a Scintillation Proximity Assay for Histone Deacetylase Using a Biotinylated Peptide Derived from Histone-H4. Anal. Biochem 1999, 267, 390-396.

Niese, S. J. Radioanal. Nucl. Chem 1999, 241, 499.

Nolin, T. D.; McMenamin, M. E.; Himmelfarb, J., Simultaneous determination of total homocysteine, cysteine, cysteinylglycine, and glutathione in human plasma by high-performance liquid chromatography: Application to studies of oxidative stress. Journal of Chromatography B 2007, 852 (1-2), 554-561.

Norris, A. J.; Sartippour, M. R.; Lu, M.; Park, T.; Rao, J. Y.; Jackson, M. I.; Fukuto, J. M.; Brooks, M. N., Nitroxyl inhibits breast tumor growth and angiogenesis. International Journal of Cancer 2008, 122 (8), 1905-1910.

O'Brien, D.; Armitage, B.; Benedicto, A.; Bennett, D.; Lamparski, H.; Lee, Y.; Srisiri, W.; Sisson, T., Polymerization of Preformed Self-Organized Assemblies. Acc. Chem. Res 1998, 31, 861-868.

Ortega-Vinuesa, J. L., Martin-Rodriguez, A. and Hidalgo-Alvarez, R., J. Colloid and Interface Sci. , 1996, 184, 259-267.

Özkan, Y.; Özkan, E.; Şimşek, B., Plasma total homocysteine and cysteine levels as cardiovascular risk factors in coronary heart disease. International Journal of Cardiology 2002, 82 (3), 269-277.

Park, S.; Imlay, J. A., High Levels of Intracellular Cysteine Promote Oxidative DNA Damage by Driving the Fenton Reaction. Journal of Bacteriology 2003, 185 (6), 1942-1950.

Paulsen, C. E.; Carroll, K. S., Cysteine-Mediated Redox Signaling: Chemistry, Biology, and Tools for Discovery. Chemical Reviews 2013, 113 (7), 4633-4679.

Peng, H.; Chen, W.; Cheng, Y.; Hakuna, L.; Strongin, R.; Wang, B., Thiol Reactive Probes and Chemosensors. Sensors 2012, 12 (11), 15907-15946.

Penttilä, K. E., Role of cysteine and taurine in regulating glutathione synthesis by periportal and perivenous hepatocytes. Biochemical Journal 1990, 269 (3), 659-664.

Pfeiffer, C. M.; Twite, D.; Shih, J.; Holets-McCormack, S. R.; Gunter, E. W., Method Comparison for Total Plasma Homocysteine between the Abbott IMx Analyzer and an HPLC Assay with Internal Standardization. Clinical Chemistry 1999, 45 (1), 152-153.

Poole, L. B., The basics of thiols and cysteines in redox biology and chemistry. Free Radical Biology and Medicine 2015, 80, 148-157.

Pullela, P. K.; Chiku, T.; Carvan III, M. J.; Sem, D. S., Fluorescence-based detection of thiols in vitro and in vivo using dithiol probes. Analytical Biochemistry 2006, 352 (2), 265-273.

Rabenstein, D. L.; Weaver, K. H., Kinetics and Equilibria of the Thiol/Disulfide Exchange Reactions of Somatostatin with Glutathione. The Journal of Organic Chemistry 1996, 61 (21), 7391-7397.

Radi, R.; Trujillo, M., Special issue on "Free Radical and Redox Biochemistry of Thiols". Free Radical Research 2016, 50 (2), 123-125.

Rapuano, R.; Carmona-Ribeiro, A., Physical Adsorption of Bilayer Membranes on Silica. J. Colloid Interface Sci 1997, 193, 104-111.

Rapuano, R.; Carmona-Ribeiro, A., Supported Bilayers on Silica. J. Colloid Interface Sci 2000, 226, 299-307.

Rohatgi, P. and Ryan, J., Chest, 1980, 78, 69-76.

Ross, E.; Bondurant, B.; Spratt, T.; Conboy, J.; O'Brien, D.; Saavedra, S., Formation of Self-Assembled, Air-Stable Lipid Bilayer Membranes on Solid Supports. Langmuir 2001, 17, 2305-2307.

Ross, E.; Rozanski, L.; Spratt, T.; Liu, S.; O'Brien, D.; Saavedra, S., Planar Supported Lipid Bilayer Polymers Formed by Vesicle Fusion. 1. Influence of Diene Monomer Structure and Polymerization Method on Film Properties. Langmuir 2003, 19, 1752-1765.

Ross, E.; Spratt, T.; Liu, S.; Rozanski, L.; O'Brien, D.; Saavedra, S., Planar Supported Lipid Bilayer Polymers Formed by Vesicle Fusion. 2. Adsorption of Bovine Serum Albumin. Langmuir 2003, 19, 1766-1774.

Schmid, A., Fujii S. and Armes S., Chem. Mater., 2007, 19, 2435-2445.

Schotanus, P., Nucl. Tracks Radiat. Meas., 1993, 21, 19-22.

(56) References Cited

OTHER PUBLICATIONS

Shao, J.; Guo, H.; Ji, S.; Zhao, J., Styryl-BODIPY based red-emitting fluorescent Off-On molecular probe for specific detection of cysteine. Biosensors and Bioelectronics 2011, 26 (6), 3012-3017.

Shibata, A.; Furukawa, K.; Abe, H.; Tsuneda, S.; Ito, Y., Rhodamine-based fluorogenic probe for imaging biological thiol. Bioorganic & Medicinal Chemistry Letters 2008, 18 (7), 2246-2249.

Singh, R. P., Gupta, N., Singh, S., Singh, A., Suman, R. and Annie, K., Bull. Environ. Contam. Toxicol., 2002, 69, 265-270.

Smith, P. A. S.; Hein, G. E., The alleged role of nitroxyl in certain reactions of aldehydes and alkyl halides. Journal of the American Chemical Society 1960, 82 (21), 5731-5740.

Son, D.; Wolosiuk, A.; Braun, P. V., Double Direct Templated Hollow ZnS Microspheres Formed on Chemically Modified Silica Colloids. Chemistry of Materials 2009, 21 (4), 628-634.

Sun, S.; Almaden, J.; Carlson, T.; Barker, J.; Gehring, M., Assay development and data analysis of receptor-ligand binding based on scintillation proximity assay. Metabolic Engineering 2005, 7, 38-44.

Svardal, A. M.; Mansoor, M. A.; Ueland, P. M., Determination of reduced, oxidized, and protein-bound glutathione in human plasma with precolumn derivatization with monobromobimane and liquid chromatography. Analytical Biochemistry 1990, 184 (2), 338-346.

Toyo'oka, T., Recent advances in separation and detection methods for thiol compounds in biological samples. Journal of Chromatography B 2009, 877 (28), 3318-3330.

Udenfriend, S.; Gerber, L.; Brink, L.; Spector, S. Proc. Natl. Acad. Sci 1985, 82, 8672.

Udenfriend, S.; Gerber, L.; Nelson, N., Scintillation proximity assay: A sensitive and continuous isotopic method for monitoring ligand/receptor and antigen/antibody interactions. Analytical Biochemistry 1987, 161 (2), 494-500.

Utsunomiya A., Watanuki T., Matsushita K., Nishina M. and Tomita I., Chemosphere, 1997, 35, 2479-2490.

Van Laer, K.; Hamilton, C. J.; Messens, J., Low-Molecular-Weight Thiols in Thiol-Disulfide Exchange. Antioxidants & Redox Signaling 2012, 18 (13), 1642-1653.

Vermeir, M.; Vanstapel, F.; Blanckaert, N. Biochem. J. 1984, 223, 455.

Vester, B.; Rasmussen, K., High Performance Liquid Chromatography Method for Rapid and Accurate Determination of Homocysteine in Plasma and Serum. cclm 1991, 29 (9), 549-554.

Wang, W.; Rusin, O.; Xu, X.; Kim, K. K.; Escobedo, J. O.; Fakayode, S. O.; Fletcher, K. A.; Lowry, M.; Schowalter, C. M.; Lawrence, C. M.; Fronczek, F. R.; Warner, I. M.; Strongin, R. M., Detection of Homocysteine and Cysteine. Journal of the American Chemical Society 2005, 127 (45), 15949-15958.

Watanabe, M. and Tamai, T., Langmuir, 2007, 23, 3062-3066.

White, P. C.; Lawrence, N. S.; Davis, J.; Compton, R. G., Electrochemically initiated 1,4 additions: a versatile route to the determination of thiols. Analytica Chimica Acta 2001, 447 (1-2), 1-10.

Winther, J. R.; Thorpe, C., Quantification of thiols and disulfides. Biochimica et Biophysica Acta 2014, 1840 (2), 838-846.

Wong, P. S. Y.; Hyun, J.; Fukuto, J. M.; Shirota, F. N.; Demaster, E. G.; Shoeman, D. W.; Nagasawa, H. T., Reaction between S-Nitrosothiols and Thiols: Generation of Nitroxyl (HNO) and Subsequent Chemistry. Biochemistry 1998, 37 (16), 5362-5371.

Wu, S.; Liu, B., Application of Scintillation Proximity Assay in Drug Discovery. Biodrugs 2005, 19 (6), 383-392.

Xia, L.; De Vries, H.; Ijzerman, A.; Heitman, L., Scintillation proximity assay (SPA) as a new approach to determine a ligand's kinetic profile. A case in point for the adenosine A1 receptor. Purinergic Signalling 2016, (12), 115-126.

Xu, H.; Aylott, J. W.; Kopelman, R., Fluorescent nano-Pebble sensors designed for intracellular glucose imaging. Analyst 2002, 127 (11), 1471-1477.

Yalow, R., Ann. Rev. Biophys. Bioeng., 1980, 9, 327-345.

Yang, B.; Furusawa, K.; Matsumura, H., Adsorption State of Egg Yolk PC Vesicles on Solid Colloidal Particles and Their Aggregation Behavior Induced by the Vesicle. Langmuir 2003, 19, 9023-9027.

Yang, X.; Guo, Y.; Strongin, R. M., Conjugate Addition/Cyclization Sequence Enables Selective and Simultaneous Fluorescence Detection of Cysteine and Homocysteine. Angewandte Chemie International Edition 2011, 50 (45), 10690-10693.

Zhukova, L.; Zhukov, I.; Bal, W.; Wyslouch-Cieszynska, A., Redox modifications of the C-terminal cysteine residue cause structural changes in S100A1 and S100B proteins. Biochimica et Biophysica Acta (BBA)—Molecular Cell Research 2004, 1742 (1-3), 191-201.

* cited by examiner

SYNTHESIS OF nanoSCINT PARTICLES

CROSS-REFERENCE TO RELATED APPLICATIONS

This application is a U.S. National Stage Patent Application under 35 U.S.C. § 371 of PCT Patent Application No. PCT/US20/35370, filed May 29, 2020, which claims the priority benefit of U.S. Provisional Application No. 62/855,240, filed May 31, 2019, all of which are incorporated herein by reference in their entirety.

FIELD OF THE INVENTION

The present invention relates to a process for producing a nanocomposite particle ("nanoSCINT particle") adapted for use in scintillating proximity assay in a relatively high quantity. The nanoSCINT particle comprises a nanoparticle organic polymer doped with at least one scintillating compound. The nanoparticle organic polymer is then encapsulated with a silica shell. In particular, the process of the invention includes adding a plurality of batch-wise portions of a polymerization initiator to an emulsion comprising a relatively high amount of polymerizable organic compound to produce a nanoparticle organic polymer, which is then doped with at least one scintillating compound, and then encapsulated with a silica shell to produce nanoSCINT particles in gram quantities in a single process.

BACKGROUND OF THE INVENTION

One of the primary challenges in developing nanoSCINT is synthesizing this material in a quantity large enough to divide and distribute to multiple labs, as well as to use throughout the course of an entire series of testing and characterization. Previously disclosed processes allowed preparation of only a few mg of nanoSCINT in a single batch and had to combine several batches to complete even a single scintillation experiment. See, for example, commonly assigned U.S. Patent Application Publication No. 2018/0118916, which is incorporated herein by reference in its entirety.

Unfortunately, even with optimization of previously disclosed process, at best only about 100 mg of nanoSCINT material could be obtained per batch, or enough for at most 1-5 experiments, depending on the design of the experiment. Though an improvement, this was still a major limitation to moving nanoSCINT forward. Such a small amount of nanoSCINT production per batch of reaction resulted in a significantly high overall cost and time in preparing a useful amount of nanoSCINT.

Therefore, there is a need for a process that can produce a significantly higher amount of nanoSCINT per reaction in order to reduce the overall material and/or labor cost as well as provide a uniform nanoSCINT that can be used in assays.

SUMMARY OF THE INVENTION

Surprisingly and unexpectedly, the present inventors have discovered that synthesizing nanoSCINT in a quantity large enough to divide and distribute to multiple labs, as well as to use throughout the course of an entire series of testing and characterization was more difficult than simple scale up process. In fact, simply scaling up the reaction conditions only led the present inventors to a few mg of nanoSCINT in a single batch. In order to conduct an entire series of testing and characterization, the reaction had to be run multiple batches and combined to complete even a single scintillation experiment. A large scale up reaction only resulted in approximately 100 mg of nanoSCINT per batch. Though an improvement, this was still a major limitation to moving nanoSCINT forward.

It was discovered by the present inventors that use of the process disclosed herein resulted in heretofore unobtainable amount of nanoSCINT in a single reaction batch. As used herein, the term "single reaction batch" refers to producing the desired nanoSCINT from start to finish without repeatedly conducting the same reaction to produce nanoSCINT and combining the nanoSCINT produced.

One particular aspect of the invention provides a process for producing a nanocomposite particle ("nanoSCINT particle") adapted for use in scintillating proximity assay, wherein said nanoSCINT particle comprises a nanoparticle organic polymer doped with at least one scintillating compound, and wherein said nanoparticle organic polymer is encapsulated with a thin layer of silica shell. The process includes:
  adding a plurality of batch-wise portions of a polymerization initiator to an emulsion comprising at least 0.1 mole/L of polymerizable organic compound and water under conditions sufficient to produce said nanoparticle organic polymer;
  adding at least one scintillating compound to said nanoparticle organic polymer to produce a nanocomposite material, wherein said nanocomposite material comprises said nanoparticle organic polymer that is doped with said scintillating compound; and
  encapsulating said nanocomposite material with a silica shell to produce said nanocomposite particle.

Another aspect of the invention provides a nanoSCINT produced by the process disclosed herein.

Still another aspect of the invention provides a nanocomposite particle ("nanoSCINT particle") adapted for use in scintillating proximity assay, wherein said nanoSCINT particle comprises a nanoparticle organic polymer doped with at least one scintillating compound, and wherein said nanoparticle organic polymer is encapsulated with a silica shell, wherein a thickness of said silica shell is about 100 nm or less.

Yet in further embodiments, processes of the invention provide improved uniformity and coating thickness of nanoSCINT. In some embodiments, it has been discovered by the present inventors that by sequential addition of initiator to the reaction mixture emulsion, at least about 5 g, typically at least about 10 g, and often at least about 15 g of nanoSCINT can be prepared in a single reaction batch, thereby narrowing the overall nanoparticle size distribution and decreasing the shell thickness by at least about 30%, typically by at least about 40%, and often by at least about 50% compared to conventional methods such as those disclosed in commonly assigned U.S. Patent Application Publication No. 2018/0118916.

DETAILED DESCRIPTION OF THE INVENTION

Some aspects of the invention provide a process for producing a nanocomposite particle ("nanoSCINT particle") adapted for use in scintillating proximity assay. The terms "nanoSCINT" and "nanoSPA" are used interchangeably herein and refer to nanocomposite particles that are adapted for use in scintillating proximity assay. In particular, nanoSCINT comprises a nanoparticle sized organic polymer core particle comprising at least one scintillator compound or material. As used herein, the term "nanoparticle" means organic polymer core particle having a mean particle size of about 1,000 nm or less, typically about 500 nm or less, often about 300 nm less, more often about 250 nm or less, and most often 150 nm or less. Still in other embodiments, $D_{90}$ particle size of the organic polymer core particle is about 900 nm or less, typically about 800 nm or less, often about 600 nm or less, more often 400 nm or less, still more often about 200 nm or less, and most often about 100 nm or less. Alternatively, the average particle size of the organic polymer core particle ranges from about 10 nm to about 1,000 nm, typically from about 5 nm to about 500 nm, often from about 10 nm to about 300 nm, more often from about 20 nm to about 250 nm, and most often from about 20 nm to about 150 nm.

The nanoSCINT also includes at least one scintillator compound. Exemplary scintillator compounds that can be used in the invention include, but are not limited to, p-terphenyl (pTP); 1,4-bis(4-methyl-5-phenyl-2-oxazolyl)benzene (dimethyl POPOP); 1-phenyl-3-(2,3,6-trimethylphenyl)-2-pyrazoline (PMP); tris(1,3-diphenyl-1,3-propanedionato)-(1,10-phenanthroline) europium (III); diphenylanthracene; 1,4-bis(5-phenyl-2-oxazolyl)benzene; 1,4-bis(2-methylstyryl)benzene; anthracene; and a combination thereof. As used herein, the term "combination thereof" means two or more, e.g., two, three, four, five, etc., of the compounds or the materials listed can be present. It should be appreciated that the scope of the invention is not limited to these particular scintillator compounds. In general, any and all known scintillator compounds can be used in the invention. The scintillator compound(s) are typically admixed or doped with, adsorbed onto, attached to, or linked to the organic polymer core particle using any of the methods known to one skilled in the art.

In one particular embodiment, the scintillating compound comprises a mixture of pTP and POPOP. In some instances, the ratio of pTP and POPOP is at least about 50:1, typically about 25:1, and often 10:1. In other instances the ratio of pTP and POPOP may be about 1:50, typically 1:25, and often 1:10.

Figure 1:
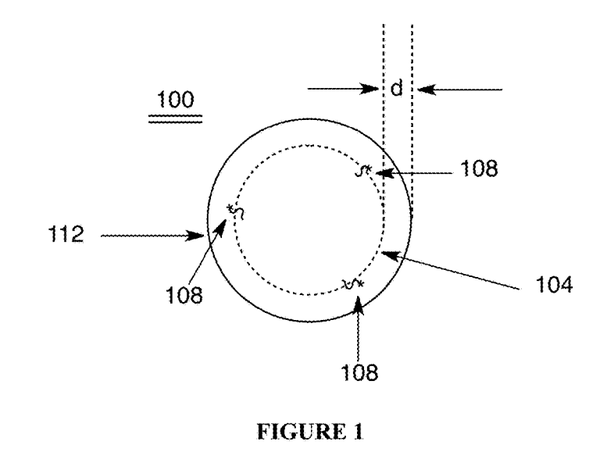
FIG. 1 is a schematic illustration of nanoSCINT 100 of the present invention.

FIG. 1 schematically illustrates a typically nanoSCINT of the invention. The nanoSCINT 100 of the invention includes a nanoparticle sized organic polymer core particle 104 comprising at least one scintillator compound or material 108. The nanoSCINT also includes a silica shell 112 of thickness d. As can be seen in FIG. 1, the silica shell 112 encapsulates nanoparticle sized organic polymer core particle 104.

As discussed in more detail below, surprisingly and unexpectedly, processes of the invention can result in a significantly thinner silica shell compared to other methods known to one skilled in the art. See, for example, U.S. Patent Application Publication No. 2018/0118916, which has been previously incorporated by reference in its entirety. In some embodiments, the thickness of silica shell is about 90% or less, typically about 80% or less, and often 75% or less of the silica shell thickness produced using conventional methods such as those disclosed in U.S. Patent Application Publication No. 2018/0118916.

Surprisingly and unexpectedly, compared to the process for producing nanoSCINT disclosed in previous methods such as those disclosed in U.S. Patent Application Publication No. 2018/0118916, processes of the invention result in a significantly higher yield of nanoSCINT and requires a significantly less amount of solvents and other materials, thereby resulting in a substantial reduction in cost and time. In general, processes of the invention result in about 100% or more, typically about 200% or more, often about 300% or more, and more often about 500% or more yield of the nanoSCINT compared to conventional methods. Furthermore, the amount of solvent required in processes of the invention is about 25% or less, typically about 50% or less, often about 75% or less, and more often about 90% or less compared to the amount of solvent required in conventional methods.

Processes of the invention include adding a plurality of batch-wise portions of a polymerization initiator to an emulsion comprising at least about 0.2, typically at least about 0.25, often at least about 0.3, and more often at least about 0.4 mole/L of polymerizable organic compound. Exemplary polymerizable organic compounds that can be used in the present invention include, but are not limited to, styrene, divinylbenzene, polyvinyltoluene, polyvinylpyrrolidone, or a combination thereof. As used herein, the term "about" when referring to a numeric value means being within an acceptable error range for the particular value as determined by one of ordinary skill in the art, which will depend in part on how the value is measured or determined, i.e., the limitations of the measurement system or the degree of precision required for a particular purpose. For example, the term "about" typically means within 1 standard deviation, per the practice in the art. Alternatively, the term "about" when referring to a numerical value can mean±20%, typically ±10%, often ±5% and more often ±1% of the numerical value. In general, however, where particular values are described in the application and claims, unless otherwise stated, the term "about" means within an acceptable error range for the particular value.

In some embodiments, the initial concentration of polymerizable organic compound in said emulsion ranges from about 0.1 mole/L to about 0.5 mole/L. In other embodiments, the ratio of said polymerizable organic compound to water is at least about 5 g per 200 mL of water.

Typical solvent used in producing the organic polymer core particles 104 comprises water. In some embodiments, the solvent used consists of water. Since the organic compound that is used to produce the organic polymer core particles 104 is typically not readily miscible with water and forms emulsion, one may add a small amount of other organic solvents to aid in solubilizing the organic compound in water. Exemplary organic solvents that can be used in solubilizing the organic compound include alcohol-based solvents, such as methanol, ethanol, isopropanol; ethers such as diethyl ether and tetrahydrofuran (THF); as well as other organic solvents such as dimethylformamide (DMF), dimethylsulfoxide (DMSO), etc. When organic solvent is used, generally the amount of organic solvent used is about 25 v/v % or less, typically about 20 v/v % or less, often about 10 v/v % or less, and most often about 5 v/v % or less relative to the amount water. However, typically no organic solvent is used, i.e., only water is used as the solvent.

In some embodiments, water is purged, e.g., with inert gas such as helium, nitrogen, or argon, to remove any dissolved oxygen. Thus, in some embodiments, the amount of dissolved oxygen in water is about 50% or less, typically about 75% or less, and often about 90% or less relative to water that has been exposed to atmosphere for at least 24 hours. Alternatively, water used in processes of the invention has about 250 ppm, typically about 100 ppm, often 50 ppm, more often 10 ppm, and most often 5 ppm or less of oxygen.

As can be seen, the concentration of polymerizable organic compound is substantially higher compared to other methods known to one skilled in the art. Typically, the polymerization initiator is added to the reaction at least two, typically at least three, often at least four, and more often at least five times during the reaction. Typically, the next portion or batch of the polymerization initiator is added about 30 min after, typically about 60 min after, and often at least 90 min after addition of the previous portion. Exemplary polymerization initiators that can be used in processes of the invention include, but are not limited to, 2,2'-azobis(2-methylpropionamidine) dihydrochloride (AIBA), 2,2'-azobis(2-methylpropionitrile) (AIBN), or a combination thereof. It should be appreciated, however, that any polymerization initiator known to one skilled in the art can be used.

The amount of each portion of the polymerization initiator added is typically about 20 mole % or less, often about 15 mole % or less, and more often about 10 mole % or less relatively to the total amount of polymerizable organic compound. Alternatively, the total amount of polymerization initiator added is typically about 50 mole % or less, often about 25 mole % or less, more often about 10 mole % or less, still more often about 5 mole % or less, and most often about 1 mole % or less relatively to the total amount of polymerizable organic compound. Still in other embodiments, the total amount of said polymerization initiator added is no more than about 1 mmol per 1,000 mmol, typically about 1 mmol per 500 mmol, and often 1 mmol per 100 mmol of said polymerizable organic compound.

Typically, the reaction temperature in the polymerization step (i.e., polymerization of polymerizable organic compound) to produce nanoparticle organic polymer is at least about 50° C., often at least about 80° C., and more often at least about 100° C. It should be appreciated that the reaction temperature is not limited to those provided herein. The reaction temperature can vary widely depending on a variety of factors such as, solvent, polymerizable organic compound, amount of polymerization initiator, polymerization initiator, etc.

The nanoparticle organic polymer produced can be concentrated prior to adding one or more scintillating compound. For example, water and any unreacted polymerizable organic compound can be removed under reduced pressure (e.g., using a rotary evaporator), by distillation, extraction, or other methods known to one skilled in the art.

The nanoparticle organic polymer is then combined or admixed with at least one scintillating compound to produce a nanocomposite material. The nanocomposite material comprises a nanoparticle organic polymer that is doped with scintillating compound(s). When two or more different scintillating compounds are used, the ratio of each scintillating compounds can vary. For example, when pTP and POPOP are used as scintillating compounds, the ratio between pTP and POPOP ranges from about 50:1, typically from about 25:1, often about 20:1, more often about 10:1, still more often about 5:1 and most often about 1:1. It should be appreciated that the scope of the invention is not limited to this particular ratio. In general any ratio of two more different scintillating compounds can be used depending on a particular assay and scintillators used. For example, in an alternative embodiment, the ratio between pTP and POPOP can range from about 1:50, typically from about 1:25, often about 1:20, more often about 1:10, and still more often about 1:5.

Doping of nanoparticle organic polymer with scintillant fluorophores typically includes dissolving scintillation compound(s) in an organic solvent such as chloroform, dichloromethane, tetrahydrofuran (THF), diethyl ether, benzene, toluene, methanol, isopropanol, ethanol, etc. This solution is then added to an aqueous mixture comprising the nanoparticle organic polymer. The resulting mixture is stirred or sonicated to produce the nanoparticle sized organic polymer core particle 104. This is typically stored as a mixture. It should be appreciated that at least a portion of the organic solvent can be removed from the reaction mixture prior to storage or the next reaction.

The process of the invention also includes encapsulating the nanoparticle sized organic polymer core particle 104 with a silica shell to produce nanoSCINT nanocomposite particle 100. For silica shell encapsulation, a concentration of at least about 10 mg/mL, typically at least about 12 mg/mL, often at least about 15 mg/mL, and more often at least about 20 mg/mL of nanoparticle sized organic polymer core particle 104 in aqueous solution is dispersed in an alcohol solvent, such as ethanol, methanol, isopropanol, or a mixture thereof. Typically, at least about 250 mL, often at least about 300 mL, more often at least about 400 mL, and most often at least about 500 mL of nanoparticle sized organic polymer core particle 104 solution is dispersed in about 2 L of an alcohol solvent. The encapsulation process also includes adding a base, e.g., ammonium hydroxide or other amine base (e.g., trialkyl amines, such as triethyl amine). Typically, excess amount of base is added relative to the amount of nanoparticle sized organic polymer core particle 104. For example, when 400 mL of 12.5 mg/mL of polystyrene nanoparticle sized organic polymer core particle 104 is encapsulate with a silica shell, about 50 mL, typically about 60 mL, often about 70 mL, and more often at least 75 mL of ammonium hydroxide is used. As can be seen, the amount of solvent used compared to those of previous methods (e.g., see, for example, U.S. Patent Application Publication No. 2018/0118916) is significantly lower, thereby greatly reducing the time and cost for synthesis of nanoSCINT of the present invention.

The silica shell encapsulation process also includes stirring the mixture for a few minutes while a silica shell precursor compound is added, typically in a dropwise manner. Exemplary silica shell precursor compounds of the invention include, but are not limited to, tetraethylorthosilicate ("TEOS"), 3-aminopropyltriethoxysilane, 3-mercaptopropyltrimethyoxysilane, or a combination thereof.

The resulting mixture is stirred for at least about 30 min, typically at least about 45 min, often at least about 60 min, and more often at least about 90 min. The nanoSCINT particles 100 that are formed are then collected, e.g., by filtration, separation, centrifugation, etc. The crude nanoSCINT particles 100 are then rinsed several times by dispersing the nanoSCINT particles 100 in water and again collecting the nanoSCINT particles 100, e.g., by filtration, separation, centrifugation, etc.

Another aspect of the invention provides a nanocomposite particle ("nanoSCINT particle") 100 that is adapted for use in scintillating proximity assay, wherein said nanoSCINT particle comprises a nanoparticle organic polymer doped with at least one scintillating compound, and wherein said nanoparticle organic polymer is encapsulated with a silica shell, wherein a thickness of said silica shell is about 200 nm or less, typically 150 nm or less, often about 100 nm or less, and more often about 50 nm or less.

In some embodiments, the concentration of nanoSCINT 100 in the solution is about 200 mg/mL or less, typically about 150 mg/mL or less, often about 100 mg/mL or less, and most often about 75 mg/mL or less.

As stated above, in some embodiments, the resulting nanoSCINT 100 of the invention have a significantly thinner silica shell compared to conventional methods, such as those described in U.S. Patent Application Publication No. 2018/0118916. In some embodiments, the silica shell thickness ("d" in FIG. 1) of nanoSCINT 100 produced using the process of the invention is about 100 nm or less, typically about 75 nm or less, often about 50 nm or less, more often about 25 nm or less, and most often about 20 nm or less. In one particular embodiment, the thickness of said silica shell is about 20 nm or less, typically about 15 nm or less, and often about 10 nm or less.

Some of the advantages of having a thinner silica shell include nanoSCINT 100 that are less dense than those produced by other methods. In some embodiments, the density of nanoSCINT 100 of the invention is about 2 g/mL or less, typically about 1.75 g/mL or less, and often about 1.5 g/mL or less.

Unlike conventional methods, a single process of the invention provides at least about 5 g, typically at least about 7.5 g, and often at least about 10 g of nanocomposite particles.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Materials: Styrene, alumina, p-terphenyl (pTP), and 1,4-bis(4-methyl-5-phenyl-2-oxazolyl)benzene (dimethyl POPOP) were purchased from Acros Organics (NJ). Tetraethylorthosilicate (TEOS), and 2,2'-azobis(2-methylpropionamidine) dihydrochloride (AIBA), 2,2'-azobis(2-methylpropionitrile) (AIBN), Triton X-100, cyclohexane, sodium citrate (tribasic) hydrate, sodium tetraborate hydrate, and 2-(N-morpholino)ethanesulfonic acid hydrate (MES) were obtained from Sigma Aldrich (St. Louis, MO). Sodium chloride, sodium phosphate hydrate (monobasic), isopropyl alcohol (IPA), chloroform, tetrahydrofuran (THF), and aqueous ammonium hydroxide (28%) were obtained from EMD Millipore (Billerica, MA). Hexyl alcohol and divinylbenzene (DVB) were purchased from Alfa Aesar (Haverhill, MA) and ethyl alcohol was purchased from Decon Laboratories (King of Prussia, PA). BioCount liquid scintillation cocktail was acquired from Research Products International (Mt. Prospect, IL). $^3$H-labeled sodium acetate was purchased from Perkin Elmer (Waltham, MA). All chemicals except styrene were used as received. Inhibitor was removed from styrene by passing the monomer through 0.5 cm diameter by 3 cm long alumina columns immediately prior to use.

Preparation of nanoSCINT Particles: Styrene (6 g, inhibitor-free) was added to 100 mL degassed $H_2O$ in an Ar-flushed 500 mL round-bottomed flask heated to 70° C. in an oil bath. Polymerization was initiated by adding 100 mg of MBA dissolved in approximately 200 of $H_2O$ to the reaction flask every 3 h for a total of 3 additions. The $H_2O$/styrene mixture was stirred rapidly for a total of 18 h. Excess styrene and some $H_2O$ were removed from the nanoparticle solution under reduced pressure using a rotary evaporator. The total volume of the nanoparticle solution was reduced to approximately 100 mL, and a small aliquot (1-2 mL) of the solution was removed and lyophilized to determine the weight per volume of nanoparticles.

Polystyrene nanoparticles were doped with scintillant fluorophores by dissolving dimethyl POPOP and of pTP in 100 mL of 1:9 isopropanol chloroform (v:v) to make 10 mM dimethyl POPOP and 100 mM pTP. Scintillant fluorophores dissolved in solvent were added directly to 500 mL of 10 mg/mL aqueous polystyrene nanoparticle solution in a 1 L round-bottomed flask. The nanoparticle solution was sonicated using a bath sonicator for several minutes to disperse organic solvent droplets throughout the $H_2O$ and the solution was stirred rapidly for at least 1 h. Organic solvents were then removed under reduced pressure using a rotary evaporator. Once solvent was removed, the scintillant fluorophore doped polystyrene nanoparticle solution was stored at room temperature until use.

Silica shells were added to scintillant fluorophore doped polystyrene nanoparticles by dispersing 400 mL of 12.5 mg/mL polystyrene nanoparticle stock solution in 2000 mL isopropanol with 75 mL $NH_4OH$. The dispersion was stirred briskly for several minutes while 20 mL TEOS was added dropwise. Stirring was continued for 1 h before nanoSCINT particles were collected by centrifugation and rinsed several times by dispersing particles in $H_2O$ and centrifuging the solution to collect rinsed particles.

Results: It was found that under some conditions, the silica shell was thinner (10-20 nm) under syntheses performed at maximum-scale (10× concentration and 10× volume) batches than in previous methods disclosed in commonly assigned U.S. Patent Application Publication No. 2018/0118916 (typically 20-50 nm, sometimes 50-100 nm), which is incorporated herein by reference in its entirety.

Figure 2:
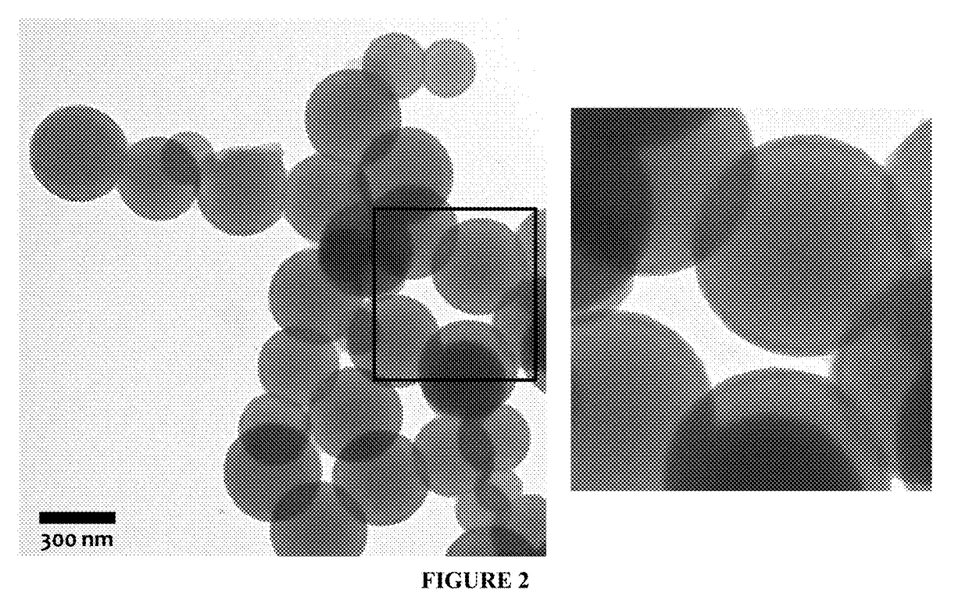
FIG. 2 is transmission electron microscopy ("TEM") image of nanoSCINT 100 produced using one embodiment of the invention. The contrast between the silica (darker) shells on the outside of the polystyrene (lighter) cores can be seen. The smaller image is an expanded view from the image enclosed within the box, in which silica shell can be more easily seen.
Figure 3:
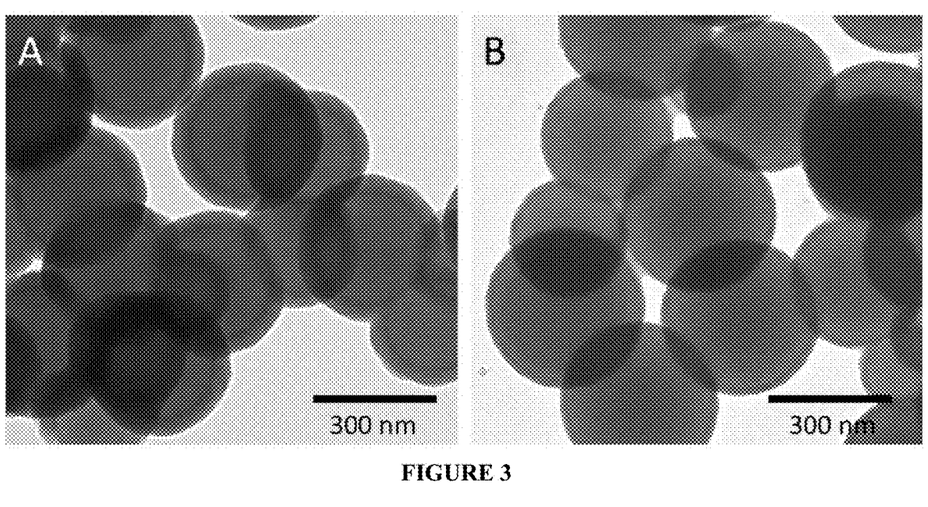
FIG. 3 is TEM images of nanoSCINT particles (A) synthesized in a batch of less than 100 mg polystyrene core nanoparticles using conventional methods, e.g., as disclosed in U.S. Provisional Patent Application No. 62/803,448, and (B) synthesized using processed disclosed herein.

Transmission electron microscopy (FIGS. 2 and 3) of the nanoSCINT particles 100 produced by the process of the present invention showed that the silica shell coverage of the polystyrene cores was complete and uniform. The decrease in shell thickness (see FIG. 3, where panel A is produced from conventional method and panel B is produced using the process disclosed herein) did not affect the function of nanoSCINT or nanoSPA. In fact, surprisingly and unexpectedly, decreased shell thickness proved to be advantageous in some situations. For example, decreasing shell thickness led to decrease in overall cost of materials. It also provided a means for controlling average nanoparticle density.

NanoSPA or nanoSCINT particles with thicker shells have a greater average density and can be used in assays where settling or collection of the nanoparticles by centrifugation of nanoSPA or nanoSCINT is beneficial. Shells can also be used as a support or attachment point for other sensor components, or to entrap components within the silica matrix. If the shell is porous, some components may reside within the pores while others, possibly different from those inside the pores, are attached to the exterior of the particle.

NanoSPA or nanoSCINT with thinner shells can stay suspended in solution for longer times without agitation and may be better suited in time-resolved assays, or for use with delicate samples. Thinner shells can also be advantageous in cases where nanoSCINT or nanoSPA are packed into columns, capillary tubing, or other enclosed spaces, where minimizing the distance between polymer cores is important.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A process for producing a gram scale of nanocomposite particle ("nanoSCINT particle") adapted for use in scintillating proximity assay, wherein said nanoSCINT particle comprises a nanoparticle organic polymer doped with at least one scintillating compound, and wherein said nanoparticle organic polymer is encapsulated with a layer of silica shell, said process comprising:
   producing said nanoparticle organic polymer by at least:
      adding a first portion of a polymerization initiator to an emulsion comprising at least 0.1 mole/L of polymerizable organic compound and water at a first time;
      adding a second portion of the polymerization initiator to the emulsion at a second time, wherein the first time is different from the second time;
      wherein the first portion and the second portion of the polymerization initiator are added under conditions sufficient to produce the nanoparticle organic polymer:
   adding at least one scintillating compound to said nanoparticle organic polymer to produce a nanocomposite material, wherein said nanocomposite material comprises said nanoparticle organic polymer that is doped with said scintillating compound; and
   encapsulating said nanocomposite material with a silica shell to produce said nanocomposite particle.

2. The process of claim 1, wherein an initial concentration of polymerizable organic compound in said emulsion ranges from about 0.1 mole/L to about 0.5 mole/L.

3. The process of claim 1, wherein said polymerizable organic compound comprises styrene, divinylbenzene, polyvinyltoluene, polyvinylpyrrolidone, or a combination thereof.

4. The process of claim 1, wherein said scintillating compound comprises p-terphenyl (pTP); 1,4-bis(4-methyl-5-phenyl-2-oxazolyl)benzene (dimethyl POPOP); 1-phenyl-3-(2,3,6-trimethylphenyl)-2-pyrazoline (PMP); tris(1,3-diphenyl-1,3-propanedionato)-(1,10-phenanthroline) europium (III); diphenylanthracene; 1,4-bis(5-phenyl-2-oxazolyl)benzene; 1,4-bis(2-methylstyryl)benzene; anthracene; or a combination thereof.

5. The process of claim 4, wherein said scintillating compound comprises a mixture of pTP and POPOP.

6. The process of claim 5, wherein a ratio of pTP and POPOP is at least about 10:1.

7. The process of claim 1, wherein said process of encapsulating with a silica shell comprises contacting said nanocomposite material with a silica shell precursor compound under conditions sufficient to produce said nanoSCINT particle comprising said thin layer of silica shell, wherein said silica shell precursor compound comprises tetraethylorthosilicate ("TEOS"), 3-aminopropyltriethoxysilane, 3-mercaptopropyltrimethyoxysilane, or a combination thereof.

8. The process of claim 1, wherein said polymerization initiator comprises 2,2'-azobis(2-methylpropionamidine) dihydrochloride (AIBA), 2,2'-azobis(2-methylpropionitrile) (AIBN), or a combination thereof.

9. The process of claim 1, wherein a ratio of said polymerizable organic compound to water is at least about 5 g per 200 ml of water.

10. The process of claim 1, wherein producing said nanoparticle organic polymer further comprises adding a third portion of the polymerization initiator to the emulsion at a third time, wherein the third time is different from the first time and the second time.

11. The process of claim 10, wherein a total amount of said polymerization initiator added is no more than about 1 mmol per 100 mmol of said polymerizable organic compound.

12. The process of claim 1, wherein a thickness of silica shell is about 50 nm or less.

13. The process of claim 1, wherein said process produces at least about 5 g of nanoSCINT particles in a single reaction batch.

* * * * *